United States Patent [19]

Jarman et al.

[11] Patent Number: 5,854,244
[45] Date of Patent: Dec. 29, 1998

[54] MELAMINE DERIVATIVES FOR USE IN THE TREATMENT OF CANCER

[75] Inventors: Michael Jarman; Helen Mary Coley, both of Sutton, Great Britain

[73] Assignee: Cancer Research Campaign Technology Limited, Regent's Park, United Kingdom

[21] Appl. No.: 631,659

[22] Filed: Apr. 2, 1996

Related U.S. Application Data

[63] Continuation of Ser. No. 313,071, Oct. 20, 1994, Pat. No. 5,534,625.

[30] Foreign Application Priority Data

Mar. 27, 1992 [GB] United Kingdom ............ 9206768
Mar. 26, 1993 [WO] WIPO ................ PCT/GB93/00625

[51] Int. Cl.⁶ .................. C07D 251/70; A61K 31/53
[52] U.S. Cl. .......................... 514/245; 544/196
[58] Field of Search ........................... 544/196

[56] References Cited

U.S. PATENT DOCUMENTS

| | | | |
|---|---|---|---|
| 2,420,157 | 5/1947 | West | 544/196 |
| 2,476,127 | 7/1949 | West | 544/196 |
| 2,476,548 | 7/1949 | Hechenbleikner | 544/196 |
| 2,485,059 | 10/1949 | Morhman et al. | 544/196 |
| 2,520,619 | 8/1950 | Wystrach et al. | 544/196 |
| 2,537,131 | 1/1951 | Grossman et al. | 544/196 |
| 2,565,194 | 8/1951 | Bacon et al. | 544/196 |
| 2,566,225 | 8/1951 | Makay et al. | 544/196 |
| 2,709,693 | 5/1955 | Widmer | 544/196 |
| 2,781,553 | 2/1957 | Varela et al. | 544/196 |

FOREIGN PATENT DOCUMENTS 0505220  9/1992  European Pat. Off. .

OTHER PUBLICATIONS

Arnould, R., et al., "Compared cytotoxicity effects of five anticancer drugs on human (HBL) and mouse (B16) melanoma cells in vitro" *Chem. Abstract* (1991) 114:23 (abstract No. 253q).

*Primary Examiner*—John M. Ford
*Attorney, Agent, or Firm*—Morrison & Foerster

[57] ABSTRACT

The present invention provides compounds of the formula (I) wherein each $R^1$, which may be the same or different, is hydrogen, $C_{1-4}$ alkyl, or an electron withdrawing group selected from the group consisting of $CF_3CH_2$ or $CH_2C\equiv CH$, $R^2$ is hydrogen, $C_{1-4}$ alkyl, or an electron withdrawing group selected from the group consisting of $CF_3CH_2$ or $CH_2C\equiv CH$. The compounds are analogs of trimelamol which have comparable activity but enhanced stability, and are useful as anticancer agents, particularly against ovarian cancer.

8 Claims, 1 Drawing Sheet

MELAMINE DERIVATIVES FOR USE IN THE TREATMENT OF CANCER

This application is a Continuation of application Ser. No. 08/313,071 filed Oct. 20, 1994, now U.S. Pat. No. 5,534,625.

This invention relates to novel 2,4,6-triaio-1,3,5-triazines, compositions containing them, processes for making them and their use in the treatment of carcinomas, particularly ovarian carcinomas.

Trimelamol [2,4,6-tris{(hydroxymethyl) (methyl) amino}-1,3,5-triazine] is clinically active, particularly against ovarian carcinomas, but its clinical development has been halted due to difficulties with formulation due to instability with respect to the formation of dimers during formulation. It has been established that the half-life of trimelamol activity in humans is short and that may limit its clinical efficacy (I. R. Judson, et al Cancer Res. 49, 5475–5479, 1989). We believe that this is, in part, due to the chemical instability of the N-hydroxymethyl functions resulting in the release of formaldehyde. We have investigated reducing the number of N-hydroxymethyl functions and stabilizing these functions using electron-withdrawing organic groups (defined in the present context as electron-withdrawing relative to methyl), with a view to lengthening the half-life and also improving amenability to formulation, for example in aqueous solutions.

Accordingly this invention provides novel 2,4,6-triamino-1,3,5-triazines having the following general formula:

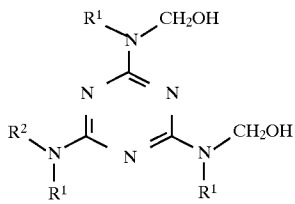

wherein each $R^1$ which may be the same or different, is hydrogen, alkyl or an electron-withdrawing group and $R^2$ is hydrogen, alkyl or an electron-withdrawing organic group. Preferably, all three groups $R^1$ are not hydrogen. The alkyl group $R^1$ and/or $R^2$ is preferably a $C_1$–$C_4$ allyl group, particularly methyl and it is preferred that all three $R^1$ groups, when alkyl, are all methyl.

Preferred electron-withdrawing organic groups are —$CH_2CF_3$ and —$CH_2C\equiv CH$. Because of the greater stability conferred on such compounds by the presence of such electron withdrawing substituents, which may constitute in lengthening the half-life and also in improving amenability to formulation, they may be prepared by allowing tris-hydroxymethyl compounds or precursors thereof to decompose in aqueous organic media and separating from the mixture of products (see FIG. 1) thus generated the appropriate compounds of the present invention, for example by chromatography on silica gel.

BRIEF DESCRIPTION OF THE DRAWING

The pathway of the reaction, by formulae, are in FIG. 1.

We have found that these new analogues of trimelamol have a similar level of activity against carcinomas, particularly ovarian carcinomas, as trimelamol, but are more stable and do not form dimers and polymers and thus are more amenable to formulation.

Figure 1:
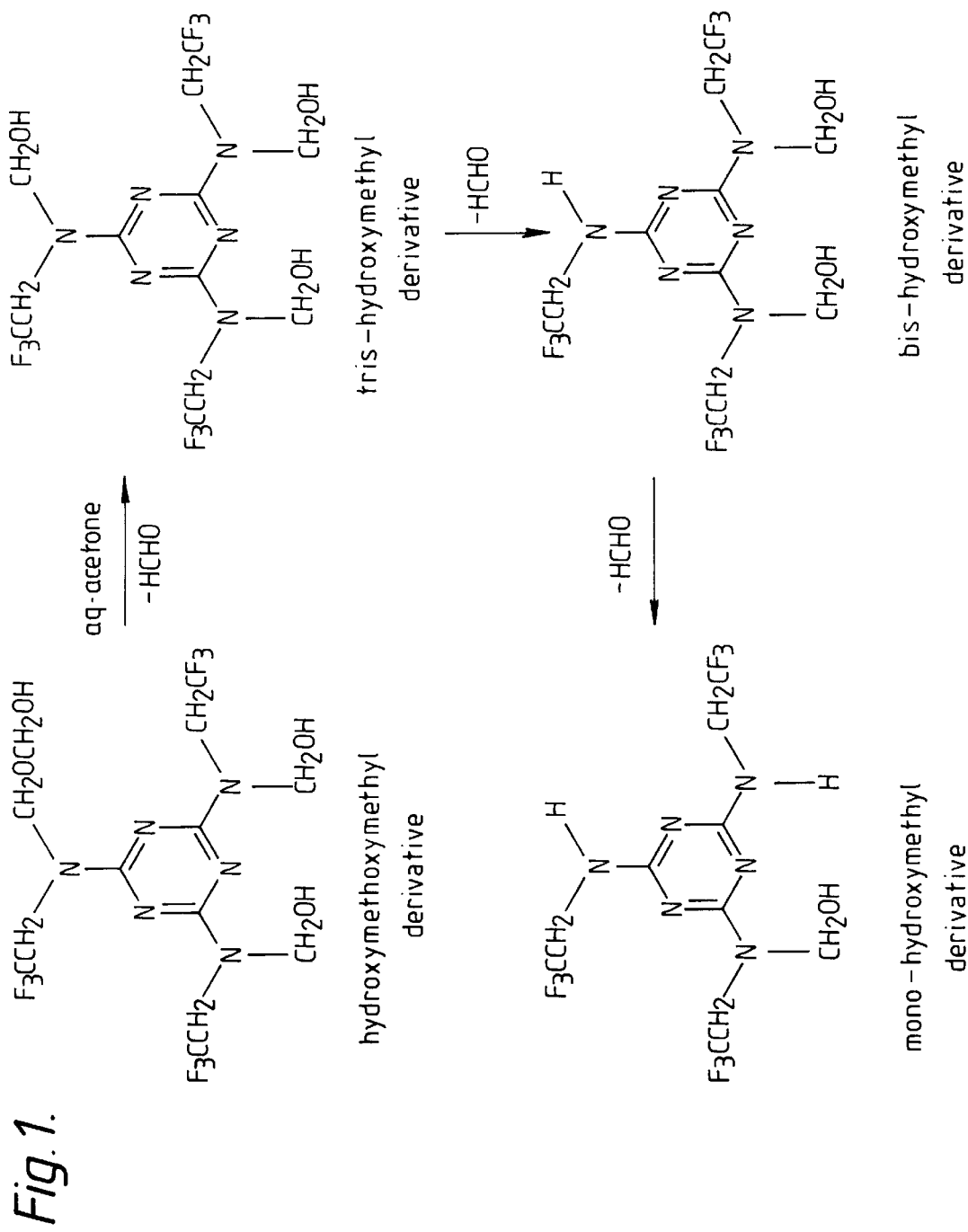

The compounds of the present invention are also prepared via novel intermediate compounds of the general formula:

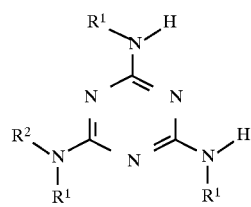

wherein $R^1$ and $R^2$ are as defined above for the formula I

The intermediates are prepared by reacting a cyanuric halide of general formula:

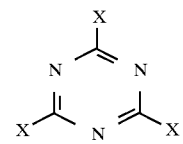

wherein X is fluoro or chloro with an amine of the formula $R^1R_2NH$ or $R^1R^2NH_2$, wherein $R^1$ and $R^2$ are as defined in formula (I), optionally in the presence of caesium fluoride.

In the absence of caesium fluoride, less than three of the substituents on the 1,3,5-triazine ring may be displaced, which allows for the preparation of asymmetrical compounds.

Treatment of the intermediates II with aqueous formaldehyde, optionally in the presence of potassium carbonate, gives the compounds of formula (I). In order to provide compounds of the formula I in which $R^1$ is methyl and $R^2$ is hydrogen, starting from compounds of the formula II in which $R^1$ and $R^2$ are also methyl and hydrogen respectively, we prefer to use a concentration of formaldehyde of from about 2 to 5% (w/v), for example about 3% (w/v). This provides a final product which contains as the major product the compound of the formula I. A small amount of the corresponding trimelamol (i.e. $R^1$=methyl, $R^2$=$CH_2OH$) and 'monomelamol' (i.e. three methyls but only one hydroxymethyl group) compounds will be produced. The presence of these compounds does not significantly affect the activity of the preparation of the compound of the invention in biological assays. However, if desired, the purity of the preparation may be increased by recrystallisation. For example, the material may be dissolved in methanol-water (eg at a ratio of 9:1), and recrystallised.

The compounds of this invention are biologically active and are of use against ovarian carcinomas, particularly against cisplatin-resistant ovarian carcinomas.

Also included within the scope of the present invention are pharmaceutical compositions which comprise, as active ingredient, at least one compound of general formula I, in association with a pharmaceutically acceptable carrier or diluent.

The compounds of the invention will normally be administered orally or by injection.

Compositions for parenteral administration will normally be solutions in aqueous saline, which is pyrogen free for human use. Such compositions can be administered intravenously or intraperitoneally.

Compositions for oral administration will mostly be in solid or liquid form, mostly as tablets, capsules, lozenges, etc. Liquid compositions can be solutions or dispersions in aqueous or non-aqueous media. Ideal solutions are of neutral or alkaline pH and of low ionic strength e.g. 5% dextrose.

Suitable daily doses of the compounds of the invention in therapeutic treatment of the human or animal body range from about 100 mg to 3 g/m² body-surface.

The following Examples illustrate the preparation of the compounds of the present invention.

EXAMPLE 1

2,4-Bis[(hydroxymethyl) (methyl) amino]6-methylamino-1,3,5-triazine

To a 3% w/v aqueous solution of formaldehyde (15 ml) was added potassium carbonate (691 mg, 5 mmol) then trimethylmelamine (841 mg, 5 mmol). The reaction mixture was stirred at room temperature until the initially clear solution (pH 11.5) became cloudy (2–3 h) then set aside overnight (16 h). The white granular solid which separated was recovered by filtration, washed with water (4×5 ml) and the product dried in vacuo over anhydrous $CaCl_2$. Yield 593 mg (52%); $^1$H-NMR spectrum $\delta_H$ ($Me_2SO$-$d_6$) 2.75 (app d, 3, $HNCH_3$), 4.99 (br s, 4, $HOCH_2$), 5.36 (br s, 2, OH) 6.61 (br s, 1, NH); mass spectrum (FAB; glycerol/thioglycerol matrix) m/z 229 ([M+H]$^+$, 70%), 211 (229-$H_2O$, 100%), 199 (229-$CH_2O$, 35 %), 181 (199-$H_2O$, 50%), 169 (199-$CH_2O$, 30%). Anal. $C_8H_{16}N_6O_2$ requires C. 42.10; H, 7.07; N, 36.82: found C, 41.87; H, 7.01; N, 36.55%.

In the Examples which follow, this compound is referred to as CB7646.

EXAMPLE 2

Further purification of title compound of Example 1

Using the procedures described in Example 1 above, but with 10 times the amount of starting materials, 6.325 g of product was obtained. HPLC analysis revealed the preparation to have the following composition: title compound: 65%, trimnelamol 22%, monohydroxymethyl derivative 12%.

This material (3 g) was dissolved in methanol-water, 9:1 (100 ml) at 37° C. and cooled at −20° C. for 24 h. The white crystalline solid was recovered by rapid filtration and dried in vacuo over anhydrous $CaCl_2$ to give 1.37 g of material having the following composition: title compound 87 % trimelamol 4 %, monohydroxymethyl derivative 9%. Signals in the $^1$H-NMR spectrum ($D_2O$, determined at 37° C.) were: title compound $\delta$3.08 ($HNCH_3$), 3.30 ($HOCH_2NCH_3$), 5.29 ($HOCH_2$); trimelamol 3.33 and 5.32; monohydroxymethyl derivative 3.05, 3.27 and 5.26.

EXAMPLE 3

2,4-Bis[(hydroxymethyl)(2,2,2 trifluoroethyl)amino]-6-(2,2,2-trifluoroethyl)amino-1,3,5-triazine A solution of 2-[([hydroxymethoxy]methyl)(2,2,2-trifluoroethyl)amino]-4,6-bis (hydroxymethyl) (2,2,2-trifluoroethyl) amino-1,3,5-triazine (500 mg, 1.02 mmol) in a mixture of acetone (3 ml) and water (2 ml) was set aside at room temperature for 18 h. Acetone was removed under vacuum and the organic materials were extracted with diethyl ether.

The organic phase was concentrated and applied to a column (50 g, 3 cm dia.) of silica gel (Merck, Art. No. 9385) which was eluted with diethyl ether. There was successively eluted 2-[(hydroxymethyl)(2,2,2-trifluoroethyl)amino]4,6-bis [2,2,2-trifluoroethyl)amino]-1,3,5-triazine (23 mg), the title compound (144 mg, 33% yield) and 2,4,6-tris [(hydroxymethyl) (2,2,2-trifluoroethyl) amino] 1,3,5-triazine (111 mg). The title compound is obtained as a white solid by trituration of the appropriate fractions with ice-cold water, recovery by filtration and desiccation in vacuo over calcium chloride. NMR spectrum: $\delta_H$($Me_2SO$-$d_6$) 4.09 (brq, 2, $F_3CCH_2NH$), 4.41 (brq. 4, $F_3CCH_2NCH_2OH$) 5.06 (d, 4, J=7.1Hz, $CH_2OH$), 5.78 (brs, 2, OH), 7.80 (brs, 1, NH). $\delta_F$−70.23, −70.03 (2s, 3, $F_3CCH_2NH$) −68.3 (s, 6, $F_3CCH_2NCH_2OH$).

In the Examples which follow, this compound is referred to as CB7683.

EXAMPLE 4

Stability of Compounds of the Invention (i) Stability in Solution

Compounds were dissolved in DMSO to a concentration of 50 mM. Aliquots were then dispersed into the appropriate medium to give a final concentration of 100 $\mu$M in a volume of about 10 ml. The diluted preparations of trimelamol and CB7646 (see Example 1) for HPLC analysis were stored in a water bath at 21°–24° C. (to simulate room temperature) or at 37° C. in water, 0.9% NaCl or 5% dextrose. Aliquots were removed from each preparation at intervals to assess their stability (i.e. half-life, $T^{1/2}$) which was measured using HPLC analysis. This entailed an isocratic elution using a mobile phase comprising 10% acetonitrile, 90% 0.05M ammonium bicarbonate. The 15 cm column was packed with C8 octyl Spherisorb material. The column was encased in a cooling cabinet which was maintained at 14°–17° C. Standards of freshly prepared solutions were run throughout the analysis period by way of controls.

$T^{1/2}$ measurements were made by measurement of the disappearance of compound by decreasing peak area with time, using a Data System 450MT2 data acquisition system (Kontron Instruments, Watford, UK) linked directly to the detector on the HPLC system (set at 225 nM). $T^{1/2}$ measurements were read from a semi-logarithmic plot of peak area (y) versus time (x).

The results are shown in table 1 and indicate that CB7646 has superior stability.

TABLE 1

| Compound | Medium | °C. | $T^{1/2}$ (Min) |
|---|---|---|---|
| Trimelamol | deionised water pH 7.5 | 37 | 120 |
| | 0.9% NaCl, pH 4.9 | r.t. | 273 |
| | 5% Dextrose, pH 4.0 | r.t. | 348 |
| CB7646 | Deionised water pH 7.5 | 37 | 180 |
| | Deionised water pH 7.5 | r.t. | 1080 |
| | 0.9% NaCl, pH 5.0 | r.t. | 960 |
| | 5% Dextrose pH 4.0 | r.t. | 1320 |

(ii) Dimer/polymer Formation in Solution

An aqueous solution of CB7646 and trimelamol in 4ml aliquots at a concentration of 4–5 mg/ml was left to stand overnight (14–16 hours) at room temperature. By the end of this period, the trimelamol solution had formed a heavy precipitate, indicative of dimer and polymer formation. Similar polymerisation of trimelamol over a period of time proved problematic during its Phase I and II clinical trials (Judson et al, 1989, Cancer Res. 49;5475–5479; Judson et al, 1991, Br. J. Cancer 63; 311–313). In contrast, preparations of CB7646 prepared in Examples 1 and 2 did not form a precipitate, indicating the monomeric form is more stable that trimelamol.

EXAMPLE 5

Cytotoxicity of Compounds of the Invention

The cytotoxicity of CB7646 and CB7683 was compared with trimelamol against mammalian tumour cell lines using the MTT assay. This assay is based upon the selective ability of living but not dead cells to reduce the tetrazolium salt MTT (3-[4,5-dimethylthiazol-2-yl]-25-diphenyl tetrazolium bromide) to purple formazan (Mosmann et al, 1983, J. Immun. Methods 65; 55–63; Carmichael et al (1987) Cancer Res. 47; 936–942). Cell lines were grown in culture with continual drug exposure. The $IC_{50}$ values (in μm) of the compounds (i.e. concentration giving 50% inhibition of cell growth as compared with untreated control) were determined, and are shown in Table 2. Figures in parenthesis refer to standard deviation or ± values for 2 or more measurements.

TABLE 2

| CELL LINE | TRIMELAMOL | CB 7646 | CB 7683 |
|---|---|---|---|
| PC6 | 12.9 (2.7) | 25.1 (2.9) | 31.6 (1.0) |
| WALKER 256 | 9.4 (0.5) | 10.7 (0.2) | ND |
| H69 | 8.5 (2.3) | 14.7 (4.9) | 8.9 (1.1) |
| CH1 | 23.4 (4.4) | 35.8 (13.1) | 40.9 (12.0) |

(ND - not done).
Cell lines used:
PC6- murine plasmacytoma
Walker 256- rat mammary carcinoma
H69 - human small cell lung cancer
CH1, 41M- human epithelial ovarian cancer
The tests on Walker 256 and H69 cells were repeated using a preparation of CB7646 prepared by the recrystallisation method of Example 2. The results were:
Walker 256 - 10.5
H69 - 16.5

EXAMPLE 6

Antitumour Activity Towards the ADJ/PC6 Tumour in Mice

The anti-tumour activity of CB 7646 prepared in accordance with Example 1 against ADJ/PC6 tumour in mice were compared with that of trimelamol. An implant of 1 $mm^3$ of tumour was made on day 1. On day 20, animals bearing tumours of comparative size were placed into groups of 4 and treated with drug on 5 consecutive days, and then left until day 30. Tumours from the treated and controls were dissected and weighed as a measure of tumour growth. Compounds were given in 5% DMSO/dextrose.

TABLE 3

% Inhibition at various Doses
(Tumour wt as % of Control Value)

| Compound | Dose (mg/kg) | | | | | |
|---|---|---|---|---|---|---|
| | 3.25 | 6.25 | 12.5 | 25 | 50 | 100 |
| CB7646 | | | | | | |
| Trimelamol | 5.6 | -1.0 | 13.7 | 5.6 | 76.8 | 98.0 |
| | 0 | 18.2 | 13.7 | 45.5 | 83.9 | 96.0 |

For CB7646 (dimelamol) the results give $LD_{50}$ > 100 mg/kg, $ED_{90}$ 74 mg/kg
Therapeutic Index (TI) > 1.4

EXAMPLE 7

Example 6 was repeated to obtain more precise $LD_{50}$ values. The $LD_{50}$, $ED_{90}$ and T.I. values were calculated and shown in Table 4.

TABLE 4

| COMPOUND | $LD_{50}$ MG/KG | $ED_{90}$ MG/KG | T.I. |
|---|---|---|---|
| TRIMELAMOL | 70 | 24 | 2.9 |
| CB 7646 | 142 | 31 | 4.6 |

EXAMPLE 8

CB7646 was tested in vivo against ovarian cancer xenografts of the PXN65 cell line transplanted into mice, substantially in accordance with Harrap et al, Annals of Oncology, 1990, 1;65–76. PXN65 is a cisplatin-sensitive line. Mice treated with either trimelamol or CB7646 showed tumour regression within 28 days whereas in untreated controls tumour growth was uncontrolled, leading to death. The results are summarised in Table 5.

TABLE 5

Activity in vivo against PXN65 Xenografts

| COMPOUND | Dose mg/kg | No. Doses | GD Days | Deaths |
|---|---|---|---|---|
| TRIMELAMOL | 30 | 5 | >273 | 0 |
| | 15 | 20 | >170 | 0 |
| CB7646 | 15 | 20 | >140 | 0 |

GD = Growth delay.
The data show that CB7646 has a comparable efficacy to trimelamol.

We claim:

1. A compound of the formula:

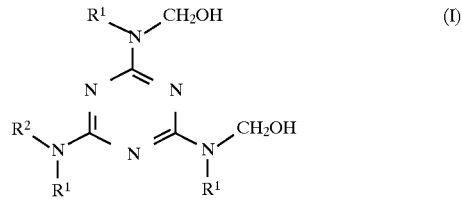

wherein each $R^1$, which may be the same or different, is hydrogen, $C_{1-4}$ alkyl or an electron withdrawing group selected from the group consisting of $CF_3CH_2$ or $CH_2C\equiv CH$, $R^2$ is hydrogen, $C_{1-4}$ alkyl or an electron withdrawing organic group selected from the group consisting of $CF_3CH_2$ or $CH_2C\equiv CH$, with the provisos that:

a) when each $R^1$ is hydrogen $R^2$ is not hydrogen, and
b) when each $R^1$ is methyl $R^2$ is not hydrogen.

2. A pharmaceutical composition comprising an active ingredient which is a compound as defined in claim 1 together with an inert diluent or carrier.

3. A process for the preparation of a compound of formula I according to claim 1 that comprises reacting a compound of the formula II

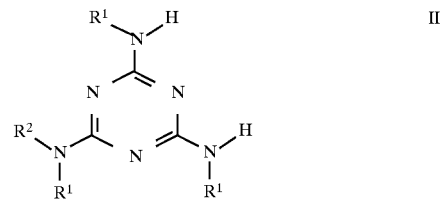

wherein in each $R^1$, which may be the same or different, is hydrogen, $C_{1-4}$ alkyl or an electron withdrawing group selected from the group consisting of $CF_3CH_2$ or $CH_2C\equiv CH$, $R^2$ is hydrogen, $C_{1-4}$ alkyl or an electron withdrawing organic group selected from the group consisting of $CF_3CH_2$ or $CH_2C{\equiv}CH$, with the provisos that:

(a) when each $R^1$ is hydrogen, $R^2$ is not hydrogen, and (b) when each $R^1$ is methyl, $R^2$ is not hydrogen.

with formaldehyde at a concentration of from 2–5% (w/v), optionally in the presence of potassium carbonate.

4. A process according to claim 3 which further comprises a recrystallisation step.

5. A method of treatment of breast cancer by tumor regression which comprises administering to a patient in need of treatment an effective amount of a compound of the formula (I).

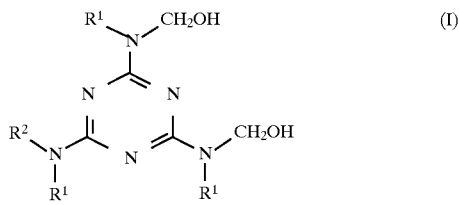

wherein each $R^1$, which may be the same or different, is hydrogen, $C_{1-4}$ alkyl or an electron withdrawing group selected from the group consisting of $CF_3CH_2$ or $CH_2C{\equiv}CH$, $R^2$ is hydrogen, $C_{1-4}$ alkyl or an electron withdrawing organic group selected from the group consisting of $CF_3CH_2$ or $CH_2C{\equiv}CH$, with the provisos that:

a) when each $R^1$ is hydrogen $R^2$ is not hydrogen, and b) when each $R^1$ is methyl $R^2$ is not hydrogen.

6. A method of treatment of ovarian cancer which comprises administering to a patent in need of treatment an effective amount of a compound of formula (I)

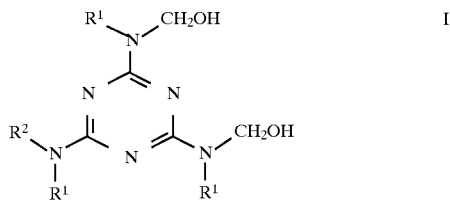

wherein each $R^1$, which may be the same or different, is hydrogen, $C_{1-4}$ alkyl or an electron withdrawing group selected from the group- consisting of $CF_3CH_2$ or $CH_2C{\equiv}CH$, $R^2$ is hydrogen, $C_{1-4}$ alkyl or an electron withdrawing organic group selected from the group consisting of $CF_3CH_2$ or $CH_2C{\equiv}CH$, with the provisos that:

(a) when each $R^1$ is hydrogen, $R^2$ is not hydrogen, and (b) when each $R^1$ is methyl, $R^2$ is not hydrogen.

7. The method according to 6 wherein said cancer is cisplatin-resistant ovarian cancer.

8. The method of claim 5 wherein the compound is administered in a dosage ranging from about 100 mg to about 3 g per $m^2$ of body surface.

* * * * *